US009731094B2

(12) United States Patent
Parker et al.

(10) Patent No.: US 9,731,094 B2
(45) Date of Patent: Aug. 15, 2017

(54) INTRODUCER SHEATH HAVING DUAL REINFORCING ELEMENTS

(75) Inventors: Fred T. Parker, Unionville, IN (US); Christopher B. Crabtree, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1510 days.

(21) Appl. No.: 12/194,723

(22) Filed: Aug. 20, 2008

(65) Prior Publication Data
US 2010/0049168 A1 Feb. 25, 2010

(51) Int. Cl.
A61M 25/00 (2006.01)

(52) U.S. Cl.
CPC ...... *A61M 25/005* (2013.01); *A61M 25/0053* (2013.01); *A61M 25/0045* (2013.01)

(58) Field of Classification Search
CPC . A61M 25/0053; A61M 25/005; A61M 25/10
USPC ........... 604/523–528, 104, 264, 123, 164.05, 604/160–161
See application file for complete search history.

(56) References Cited

U.S. PATENT DOCUMENTS

| 5,002,041 | A | | 3/1991 | Chikama ........................ 128/4 |
| 5,380,304 | A | | 1/1995 | Parker ........................... 604/282 |
| 5,702,373 | A | * | 12/1997 | Samson ........................ 604/527 |
| 5,792,124 | A | | 8/1998 | Horrigan et al. ............. 604/282 |
| 6,152,912 | A | * | 11/2000 | Jansen et al. ................. 604/526 |
| 6,159,187 | A | * | 12/2000 | Park et al. .................... 604/264 |
| 6,159,198 | A | | 12/2000 | Gardeski et al. ............. 604/523 |
| 6,165,163 | A | | 12/2000 | Chien et al. .................. 604/623 |
| 6,699,274 | B2 | | 3/2004 | Stinson ........................ 623/1.12 |
| 6,726,712 | B1 | * | 4/2004 | Raeder-Devens et al. .. 623/1.11 |
| 6,939,337 | B2 | * | 9/2005 | Parker et al. ................. 604/528 |
| 7,025,758 | B2 | | 4/2006 | Klint ............................ 604/524 |

(Continued)

FOREIGN PATENT DOCUMENTS

| WO | WO 96/33763 A2 | 10/1996 | ............ A61M 25/00 |
| WO | WO 01/66176 A1 | 9/2001 | ............ A61M 25/00 |

(Continued)

OTHER PUBLICATIONS

Scheirs, J.; Burks, S.; Locaspi, A. Trends Polym. Sci.1995, 3, 74.*

(Continued)

*Primary Examiner* — Edelmira Bosques
(74) *Attorney, Agent, or Firm* — Brinks Gilson & Lione (57) ABSTRACT

An introducer sheath for deploying a stent to a target site within a body passageway of a patient. The introducer sheath includes a tubular inner liner having a proximal portion, a distal portion, and an outer surface. A first reinforcing element, and a second reinforcing element are positioned along the outer surface of the inner liner. The first reinforcing element comprises a braid the second reinforcing element comprises a coil. The braid is positioned at the proximal portion of the inner liner and extends distally therefrom. The coil is positioned at the distal portion longitudinally adjacent the braid. The braid has a length that may extend about 90% of the length of the sheath. An outer jacket is positioned longitudinally around the reinforcing elements, and is connected to the inner liner between the respective wires of the braid and the coil.

20 Claims, 3 Drawing Sheets

(56) References Cited

U.S. PATENT DOCUMENTS

| | | | |
|---|---|---|---|
| 7,217,769 B2* | 5/2007 | Zamora et al. | 525/404 |
| 2001/0034514 A1* | 10/2001 | Parker | 604/525 |
| 2002/0032408 A1* | 3/2002 | Parker et al. | 604/103.09 |
| 2003/0050686 A1* | 3/2003 | Raeder-Devens et al. | 623/1.11 |
| 2003/0135198 A1* | 7/2003 | Berhow et al. | 604/524 |
| 2004/0220549 A1 | 11/2004 | Dittman et al. | 604/526 |
| 2006/0095050 A1* | 5/2006 | Hartley et al. | 606/108 |
| 2006/0100687 A1 | 5/2006 | Fahey et al. | 623/1.11 |
| 2006/0259118 A1 | 11/2006 | Pal et al. | 623/1.11 |
| 2007/0060996 A1 | 3/2007 | Goodin et al. | 623/1.11 |
| 2007/0208405 A1* | 9/2007 | Goodin et al. | 623/1.11 |
| 2007/0276354 A1 | 11/2007 | Osborne | 604/527 |
| 2008/0051761 A1* | 2/2008 | Slazas et al. | 604/527 |

FOREIGN PATENT DOCUMENTS

| | | | | |
|---|---|---|---|---|
| WO | WO 02/05885 A2 | 1/2002 | | A61M 25/00 |
| WO | WO 2008/130740 A1 | 10/2008 | | A61M 25/00 |

OTHER PUBLICATIONS

Breslow, D. S.; Hulse, G. E.; Matlack, A. S. J. Am. Chem. Soc. 1957, 79, 3760; Matlack, A. S. U.S. Pat. No. 2,672,480, 1954, assigned to Hercules Powder Co.*

John Scheirs, Fluoropolymer Coatings, ExcelPlas Australia, REtrieved from Polymeric Materials Encyclopedia on Mar. 31, 2009.*

Junzo Masamoto, Nylon 3, Polymer Development Laboratory Asahi Chemical Industry Company, Ltd. Retrieved from Polymeric Materials Encyclopedia on Mar. 31, 2009.*

* cited by examiner

FIG. 4

INTRODUCER SHEATH HAVING DUAL REINFORCING ELEMENTS

BACKGROUND

1. Technical Field

This invention relates to the field of medical introducer apparatuses, and more particularly, to a medical introducer apparatus having longitudinally adjacent braid and coil reinforcing elements.

2. Background Information

Numerous advances of considerable note have occurred in medical surgical techniques over the last few decades. Among the most significant advances has been the adoption, and now-routine performance, of a wide variety of minimally invasive procedures. Non-limiting examples of such procedures include angioplasty, endoscopy, laparoscopy, and arthroscopy. These minimally invasive procedures can be distinguished from conventional open surgical procedures in that access to a site of concern within a patient is achieved through a relatively small incision, into which a tubular device (or tubular portion of a device) is inserted or introduced. The tubular device, or device portion, keeps the incision open while permitting access to the target site via the interior (i.e., lumen) of the tubular device.

Body passageways in which medical interventional devices are now commonly introduced include the esophagus, trachea, colon, biliary tract, urinary tract, and vascular system, among other locations within the body. One particularly significant example of a minimally invasive technique involves the temporary or permanent implantation of a medical interventional device, such as a stent, into a passageway in the body of a patient.

When placing the medical interventional device, communication with the passageway is typically attained by inserting an access device, such as an introducer sheath, into the body passageway. One typical procedure for inserting the introducer sheath is the well-known Seldinger percutaneous entry technique. In the Seldinger technique, a needle is initially inserted into the passageway, such as a vessel, and a wire guide is inserted into the vessel through a bore of the needle. The needle is withdrawn, and an introducer assembly is inserted over the wire guide into the opening in the vessel.

Typically, the introducer assembly includes an outer introducer sheath, and an inner dilator having a tapered distal end. The tapered end of the dilator stretches the opening in the vessel in controlled fashion, so that introduction of the larger diameter introducer sheath may then be carried out with a minimum of trauma to the patient. Following satisfactory placement of the introducer sheath, the dilator is removed, leaving at least the distal portion of the larger diameter introducer sheath in place in the vessel. The interventional device, such as an expandable stent, etc., may then be inserted through the introducer sheath for placement at a target site within the vasculature. Alternatively, the stent may be placed at the target site by withdrawing the introducer sheath from around the constricted stent. In either technique, upon placement at the target site, the stent expands to the diameter of the vessel.

Historically, percutaneous insertion techniques were problematic, due at least in large part to the lack of flexibility and/or kink resistance of the sheath. Early sheaths were typically formed of a relatively stiff fluorocarbon, such as polytetrafluoroethylene (PTFE) or fluorinated ethylene propylene (FEP). The sheaths were typically of thin-walled construction, and were prone to kinking, particularly when threaded through tortuous pathways within the body. Increasing the thickness of the sheath only minimally improved the kink resistance of the sheath. At the same time, the added thickness occupied valuable space in the vessel, thereby minimizing the diameter of the interventional device that could be passed therethrough. In addition, increasing the thickness of the sheath necessitated the use of a larger entry opening than would otherwise be required.

A kinked sheath is essentially unusable, and generally cannot be straightened while positioned in the body of the patient. Consequently, once a sheath kinks, the sheath must be removed from the vessel, leaving an enlarged, bleeding opening which cannot generally be reused. Access to the vessel must then be re-initiated at an alternative site, and the process repeated with a new sheath. In some cases, a suitable alternative site is not available, and the percutaneous procedure must be abandoned altogether in favor of a different, and often more intrusive, technique.

In recent years, introducer sheaths have been improved in order to enhance their flexibility and kink resistance. Such sheaths are now routinely used to percutaneously access sites in the patient's anatomy that previously could not be accessed with existing sheaths, or that could be accessed only upon the exercise of an undesirable amount of trial and error, with the concomitant discard of sheaths whose placement had been unsuccessful.

Many newer sheaths exhibit a much higher degree of kink resistance than was achievable with prior art sheaths. One example of a flexible, kink resistant introducer sheath is described in U.S. Pat. No. 5,380,304. The sheath described in this patent includes a lubricious inner liner having a helical coil fitted over the liner. An outer tube is connected to the outer surface of the liner through the coil turns. The coil reinforcement imparts kink resistant to this thin-walled sheath through a wide range of bending.

U.S. Patent Publication No. 2001/0034514 discloses an introducer sheath similar in many respects to the sheath of the '304 patent. The sheath in the patent publication is formed such that the proximal end of the sheath has a higher stiffness, while the distal end has a lower stiffness. Since the distal portion of the sheath has a lower stiffness (and therefore is more flexible) than the proximal portion, the sheath is able to traverse portions of the anatomy that would have been difficult, if not impossible, to traverse with stiffer sheaths. Since the proximal portion has a higher stiffness (and is therefore less flexible) than the distal portion, the sheath maintains the trackability to traverse tortuous areas of the anatomy. This presence of the coil reinforcement also enables this sheath to be kink resistant through a wide range of bending angles. These patent documents are incorporated by reference herein.

The development of introducer sheaths, such as those described above, has revolutionized the practice of medicine, and in particular, the ability of the physician to introduce medical interventional devices into target sites without the necessity of carrying out conventional open surgical operations. The percutaneous methods described are generally less expensive than the open surgical methods previously employed, are less traumatic to the patient, and typically require a shorter recovery time.

Notwithstanding the benefits that have been achieved by the use of such introducer sheaths, new challenges continue to be faced. For example, as noted above, introducer sheaths are frequently used for delivering an expandable device, such as a stent, filter, basket, etc., to a target site within a body passageway of a patient. In many such cases, these devices are placed (in constricted form) in the interior passageway of the sheath. Once the introducer sheath is properly positioned at the target site, the sheath is withdrawn from around the constricted device. Typically, an inner catheter (e.g., pusher) positioned in the lumen of the sheath prevents the device from withdrawing with the sheath. Upon withdrawal of the sheath, the device radially expands to the diameter of the body passageway at the target site.

Deployment of expandable devices, such as stents, in this manner is now a routine practice, and such deployment is often carried out with only a minimum of complications, if any. However, when devices such as coated and/or relatively long (e.g., at least about 80 mm in length) stents are placed in a sheath passageway in this manner for delivery, a high deployment force may be required due to the outward force exerted by such stents on the interior wall of the sheath. In this event, the coiled introducer sheath has a tendency to stretch longitudinally as it is withdrawn from around the stent. Although this phenomenon may also occur with non-coated stents or shorter stents, it is more pronounced with the coated and/or longer stents. Due to the extra diameter and/or length of these stents, a greater push force must typically be imparted by the inner catheter to overcome the tendency of these stents to remain with the sheath, as the sheath is withdrawn from the passageway. As a result, as the sheath is withdrawn over the stent, the resistance imparted by the stent may cause such sheaths to longitudinally stretch upon withdrawal.

Although such stretching may have no practical significance when shorter stents are positioned within the sheath, with longer stents, the stretching of the sheath causes the distance between adjacent turns of the coil to increase. This longitudinal expansion of the reinforcing coil adversely affects the ability of the sheath wall to withstand the radial expansive forces exerted on the interior of the wall by the stent. In addition, in some cases, the frame of the stent is able to push into this expanded distance between coil turns. When this occurs, a pocket may be created in the inner wall of the sheath. When the stent is disposed in this pocket, even more resistance is imparted upon the sheath upon withdrawal from the stent.

It is desired to provide an improved introducer apparatus suitable for traversing tortuous passageways in the patient's anatomy, and that is capable of minimizing the problems of the prior art. More particularly, it is desired to provide an introducer sheath that is capable of minimizing elongation or stretching during withdrawal of the sheath, thereby providing for more efficient withdrawal of the sheath when used to position a medical interventional device, such as an elongated stent, in a body passageway.

BRIEF SUMMARY

The problems of the prior art are addressed by the features of the present invention. In one form thereof, the invention comprises an introducer sheath suitable for use in deploying a medical interventional device, such as a stent, to a target site within a body passageway of a patient. The introducer sheath includes a tubular inner liner having a proximal portion, a distal portion, and an outer surface. A first reinforcing element, and a second reinforcing element are positioned along the outer surface of the inner liner. The first reinforcing element comprises a braid and the second reinforcing element comprises a coil. The braid is positioned at the proximal portion of the inner liner and extends distally therefrom. The coil is positioned at the distal portion longitudinally adjacent the braid. The braid has a length that extends at least about 50%, preferably at least 70%, and more preferably 90% of the length of the sheath. An outer jacket is positioned longitudinally around the reinforcing elements, and connected to the inner liner.

In another form thereof, the invention comprises an introducer sheath for use in deploying a medical interventional device to a target site within a body passageway of a patient. The introducer sheath includes a tubular inner liner having a proximal portion, a distal portion, and an outer surface, wherein the tubular inner liner comprises a fluoropolymer such as PTFE. The inner liner has a lumen extending therethrough sized for receiving the medical interventional device therein. The distal portion defines a nesting area for maintaining the medical interventional device prior to deployment thereof. A first reinforcing element is positioned along the outer surface of the inner liner, wherein the first reinforcing element is disposed at the proximal portion of the inner liner and extends in a distal direction therefrom. The first reinforcing element comprises a braid formed of a plurality of interwoven filaments, and having a length that extends at least about 70% of the length of the introducer sheath. A second reinforcing element is positioned longitudinally adjacent and distal to the first reinforcing element along the outer surface of the inner liner. The second reinforcing element comprises a helical coil having a length substantially equal to the length of the nesting area. An outer jacket is positioned longitudinally around the first and second reinforcing elements, and is connected to the outer surface of the inner liner between the interwoven filaments and the coil turns.

In yet another form thereof, the invention comprises a method of delivering a medical interventional device to a target area in a body passageway of a patient. An introducer sheath comprises a tubular inner liner having a proximal portion, a distal portion, and an outer surface. The tubular inner liner comprises a fluoropolymer, and has a lumen sized for receiving the medical interventional device extending therethrough. The distal portion defines a nesting area for maintaining the medical interventional device prior to deployment. A first reinforcing element is positioned along the outer surface of the inner liner, the first reinforcing element being disposed at the proximal portion of the inner liner and extending in a distal direction therefrom. The first reinforcing element comprises a braid formed of a plurality of interwoven filaments, and has a length that extends at least about 70% of the length of the introducer sheath. A second reinforcing element is positioned longitudinally adjacent and distal to the first reinforcing element along the length of the introducer sheath. The second reinforcing element comprises a helical coil having a length substantially equal to the length of the nesting area. An outer jacket is positioned longitudinally around the first and second reinforcing elements, and is connected to the outer surface of the inner liner between the interwoven filaments and the coil turns. A medical interventional device, such as a stent, is positioned in the lumen at the nesting area. The sheath is inserted into the body passageway such that the distal end portion of the sheath is disposed at the target area. The medical interventional device is delivered to the target area from the sheath distal end portion.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

Figure 1:
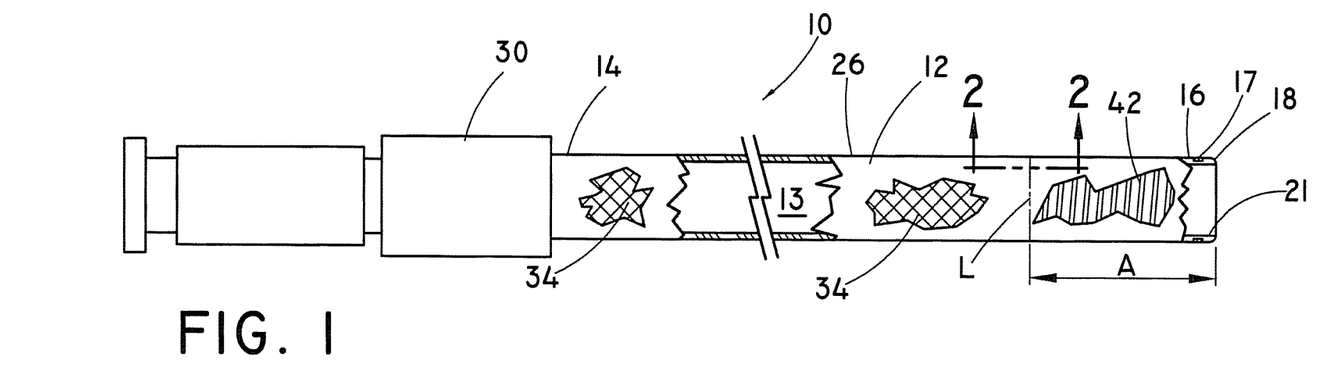
FIG. 1 is a side view, partially in section, of an introducer sheath according to an embodiment of the present invention.

FIG. 1 illustrates an introducer sheath 10 according to an embodiment of the present invention. Introducer sheath 10 includes a tubular sheath body 12 having a passageway 13 extending longitudinally therethrough. Tubular body 12 includes a proximal portion 14, and a distal portion 16 for initial insertion into the body passageway. In the non-limiting embodiment shown, the proximal end of tubular sheath body 12 is receivable in a base structure, such as a guide catheter 30. Those skilled in the art will appreciate that various other conventional proximal attachments, such as a hub or a multi-chamber manifold, may alternatively be used to receive the proximal end of tubular sheath body 12. Two reinforcing members, namely a braid 34 and a coil 42, are disposed along the length of sheath body 12 in a manner to be described. If desired, a conventional radiopaque marker band 17 may be incorporated into the distal portion 16 of the sheath in well-known fashion.

Figure 2:
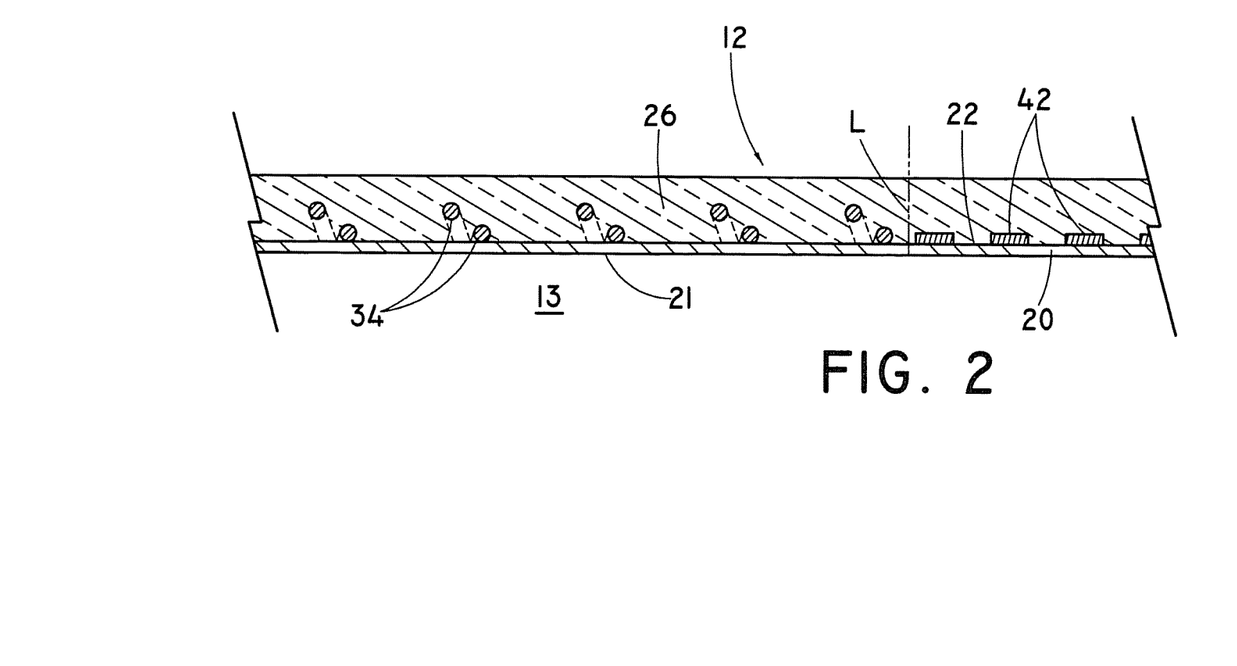
FIG. 2 is a partial longitudinal cross-sectional view of a portion of the wall of the introducer sheath of FIG. 1.

FIG. 2 is a longitudinal cross-sectional view of a portion of the wall of tubular sheath body 12 of introducer sheath 10. This figure best illustrates the layered structure of the sheath body, and the relative positions of the dual reinforcing members. As illustrated, sheath body 12 comprises an inner liner 20, and the dual reinforcing members fitted around inner liner 20. In this embodiment, the dual reinforcing members comprise braid 34 beginning at or near the proximal end of the inner liner and extending the majority of the length (e.g., about 90%) of the inner liner, and coil 42 extending substantially over the remaining length of the inner liner at the distal end. A polymeric outer jacket 26 is mechanically connected to the radially outer surface 22 of inner liner 20 through the spaced filaments of the braid 34 or between the turns of the coil 42.

Inner liner 20 preferably comprises a lubricious material, and more preferably, a fluoropolymer of the type commonly used to impart strength and lubricity to a medical device. Most preferably, the fluoropolymer comprises polytetrafluoroethylene (PTFE). Lubricious inner liners for sheaths are well known in the medical arts, and those skilled in the art can readily select an appropriate liner for a particular use. It is envisioned that inner liner 20 can have a uniform inside diameter ranging up to about 30 French (10 mm), or even higher in some instances. The wall thickness of inner liner 20 will typically range between about 0.001 and 0.003 inch (0.0254 and 0.076 mm), and is preferably about 0.0015 inch (0.038 mm). Even larger, or smaller, wall thicknesses may be appropriate in a particular case. Those skilled in the art will appreciate that all dimensions recited herein are exemplary only, and that the apparatus described herein may be constructed to be of any size necessary and appropriate to accomplish the purposes for which the sheath is to be employed.

Preferably, the inner diameter of inner liner 20 is uniform the entire length of passageway 13, thereby allowing passage of the largest possible diameter medical interventional device therethrough. The lubricious PTFE material presents a slippery inner surface 21 to allow easy insertion and withdrawal of the medical interventional device. Inner surface 21 is also smooth and nonporous for minimizing the formation of blood clots and other thrombi thereon. The wall of the inner liner 20 should have sufficient radial rigidity to prevent the turns of braid 34 and coil 42 from protruding into passageway 13.

As stated, outer jacket 26 is mechanically connected to the outer surface 22 of the inner liner 20 through the spacings of respective filaments of the braid 34, or through the turns of the coil 42. Preferably, outer surface 22 of the inner liner 20 is chemically etched or mechanically roughened in well-known manner for enhancing bonding between the liner and the outer jacket. Outer tube jacket 26 may be formed of any well-known polymer commonly used for such purpose. Preferably, outer jacket 26 comprises a heat formable polyamide material, such as nylon, or a polyether block amide (PEBA). This heat formable material melts upon heating, such that portions flow between the respective filaments or turns of the braid or the coil, and bond to the roughened outer surface of the inner liner.

Braid 34 comprises a plurality of crossed wires of circular, flat, elliptical, or other conventional wire cross-section (circular being illustrated in FIG. 2). Preferably, braid 34 is formed of medical grade metal or metal alloy. Non-limiting examples of such materials include stainless steel, and shape memory alloys such as nitinol, a nickel-titanium alloy. Those skilled in the art will appreciate that braid 34 may alternatively be formed of other medical grade materials known in the art to be suitable for such use, such as polymers and composite materials. The braid may be formed with varied numbers, and pitches, of crossed wires, which number of wires and pitch may be varied within segments of a particular sheath, all in accordance with known techniques. Braids are well-known reinforcements for medical devices, and those skilled in the art are well aware of suitable techniques for applying a braided structure to a tubular member for medical applications.

As with the braid described above, coil 42 may comprise a medical grade metal or metal alloy, such as stainless steel, or a shape memory composition such as nitinol. Alternatively, coil 42 may be formed from other medical grade materials known in the art to be suitable for such use. Preferably, coil 42 is formed from flat wire as shown in FIG. 2, although a coil formed from other compositions and having other cross-sections may be substituted in an appropriate case. As described herein, coil 42 may be wrapped, wound, compression fitted, or otherwise applied around inner liner 20 in conventional fashion. As with braids, coils are also well-known reinforcements for medical devices, and those skilled in the art are well aware of suitable techniques for applying a coil to a tubular member for medical applications.

Although braided and coiled reinforcements are now routinely used as reinforcements in tubular medical devices, those skilled in the art recognize that these reinforcements are not generally considered interchangeable. Rather, each is generally preferred in order to address a particular condition likely to be encountered by the sheath during introduction into a body opening. For example, a coiled reinforcement is typically utilized in a sheath to minimize the possibility of the sheath kinking, and/or to minimize ovalization of the sheath lumen during bending of the sheath.

As stated previously, such sheaths are frequently used to access tortuous passageways in the vasculature of a patient for the deployment therethrough of a medical interventional device, such as a stent. In order to make the most efficient use of the sheath, the stent or other medical interventional device housed therein will preferably have an outer diameter that is as close as reasonably possible to the inner diameter of the sheath. During deployment of the interventional device from the sheath, the sheath must often traverse a bend in a body passageway of at least 60°, and often much greater than this. During this time, the lumen of the sheath should maintain its rounded cross-section to the greatest extent possible, so that the interventional device can pass through the lumen of the sheath upon delivery to the target site. Anything other than minimal kinking or ovalization of the sheath lumen can prevent passage of the device, thereby rendering the sheath unsuitable for its intended purpose in some instances.

A braid reinforcement, on the other hand, is typically utilized when it is desired to impart stiffness, pushability, or torqueability to the sheath. Such properties are advantageous when maneuvering a lengthy sheath or catheter into remote anatomy. A braid reinforcement, however, is not generally capable of providing the type of kink resistance available with a coil. Similarly, a coil reinforcement is not generally capable of providing the type of pushability or torqueability available with a braid.

Although each of these types of reinforcements has its advantages as described, the ability to resist kinking and ovalization throughout a large bending radius is often considered a paramount property of a sheath. This is particularly true in the vicinity of the distal end of the sheath. For this reason, it is believed that most presently-available commercial introducer sheaths include a coil reinforcement. Examples of such sheaths having coil reinforcements are described in the incorporated-by-reference patent documents recited hereinabove. Since the proximal portion has a higher stiffness (and is therefore less flexible) than the distal portion, the sheath maintains the traceability to traverse tortuous areas of the anatomy.

When sheaths having a coil reinforcement are used to deploy stents having a comparatively short length (e.g., less than about 80-100 mm), such deployments may often be carried out without undue complication. The relatively short length of the stent, most of which are less than about 80 mm in length, typically provides minimal resistance to the interior of the sheath upon deployment.

When comparatively longer stents (e.g., greater than 80-100 mm in length) are deployed from prior art sheaths, however, the deployment of the stent from a sheath having a coil reinforcement may be less than optimal. Due to the greater length of these stents, a greater aggregate outward force is exerted by the stent upon the interior wall of the sheath, when compared to the force exerted by a stent of a lesser length. As a result, a higher push force must typically be imparted by the inner catheter to overcome the tendency of the stent to remain with the sheath as the sheath is withdrawn from the passageway. This phenomena may also occur upon the deployment of coated stents from the sheath. This is due to the increased forces exerted against the wall of the sheath by the larger diameter coated stent when compared to an otherwise similar, but uncoated, stent.

The resistance imparted by the stent upon the interior wall of the coiled sheath upon deployment may cause the coil, and therefore the sheath, to stretch in the longitudinal direction as the sheath is withdrawn from around the stent. Although such stretching may have little practical significance when smaller stents are positioned within the sheath, with longer stents this increase in the distance between adjacent coil turns may limit the practical effectiveness of this reinforcing member.

Typically, the coil functions as a reinforcing jacket of sorts to enable the sheath to withstand the radially outwardly directed forces exerted by the constricted stent within the sheath. As the sheath is stretched, the distance between adjacent coil turns is increased, thereby limiting the ability of the coil to reinforce the sheath. As a result, the ability of the sheath to withstand the radial expansive forces exerted on the interior of the wall by the stent is diminished. In some cases, the frame of the stent may even be able to radially push into this expanded distance between coil turns, thereby creating one or more pockets in the inner wall of the sheath that receive the expanded stent frame portion. When the stent frame portion is disposed in such pockets, an even greater pull force must typically be imparted on the sheath to overcome the tendency of the stent to remain with the sheath upon withdrawal of the sheath.

This phenomenon is not exclusive to the use of longer stents, and may occur when deploying stents less than 80-100 mm in length. However, the effect is generally more pronounced with longer stents, and/or with coated stents of any length wherein the additional diameter imparted to the stent by the coating requires additional forces upon deployment. Furthermore, the effect typically increases with the length of the stent being deployed, and/or with the amount of the coating. Thus, for example, the effect is generally more pronounced with a stent having a length of 200 mm when compared to a length of 100 mm; with a stent having a length of 300 mm when compared to a stent having a length of 200 mm, etc.

Contrary to the prior art sheaths described above, the inventive sheath is provided with a braid reinforcement along a portion of the length of the sheath body, and preferably, along a majority of its length. Beginning at or near the proximal end of the sheath body, the braid extends over at least 50% of the length of the sheath body, preferably at least 70% of the length of the sheath body, and more preferably at least 90% of the length of the sheath body. The coil is positioned longitudinally adjacent to the braid, in the distal direction. The relative lengths of the braid and coil may vary in a particular case, but a salient consideration is that the coil will be long enough to cover all, or most, of the length of the underlying stent or other device when positioned in the distal portion of the sheath body.

In a particularly preferred embodiment, the braid starts at or near the proximal end of the sheath and extends substantially to the area of the proximal end of the inserted stent. The coil starts at this stent proximal end and extends substantially to the distal end of the sheath body, or alternatively, to the location of a distal marker band that may be provided substantially adjacent the distal end. Thus, for example, when the braid extends over at least 50% of the length of the sheath body as described, the longitudinally adjacent coil has a length that does not exceed 50% of the length of the sheath. When the braid extends over at least 70% of the length of the sheath body, the longitudinally adjacent coil has a length that does not exceed 30% of the length of the sheath. When the braid extends over at least 90% of the length of the sheath body, the longitudinally adjacent coil has a length that does not exceed 10% of the length of the sheath.

The (imaginary) line of demarcation between the braid and the coil is marked by "L" in FIGS. 1 and 2. Those skilled in the art will appreciate that this line may be positioned anywhere along the minor length of sheath body 12 (meaning less than 50% of the length of the sheath), but is typically aligned such that at least about 70%, and preferably at least 90%, of the length of sheath body 12 is proximal (to the left in the orientation of FIGS. 1 and 2) of line L. Thus, for example, when the braid extends over at least 50% of the length of the sheath body to line of demarcation "L", the longitudinally adjacent coil at the other side of line of demarcation "L" has a length that does not exceed 50% of the length of the sheath. When the braid extends over at least 70% of the length of the sheath body, the longitudinally adjacent coil has a length that does not exceed 30% of the length of the sheath. When the braid extends over at least 90% of the length of the sheath body, the longitudinally adjacent coil has a length that does not exceed 10% of the length of the sheath.

Figure 4:
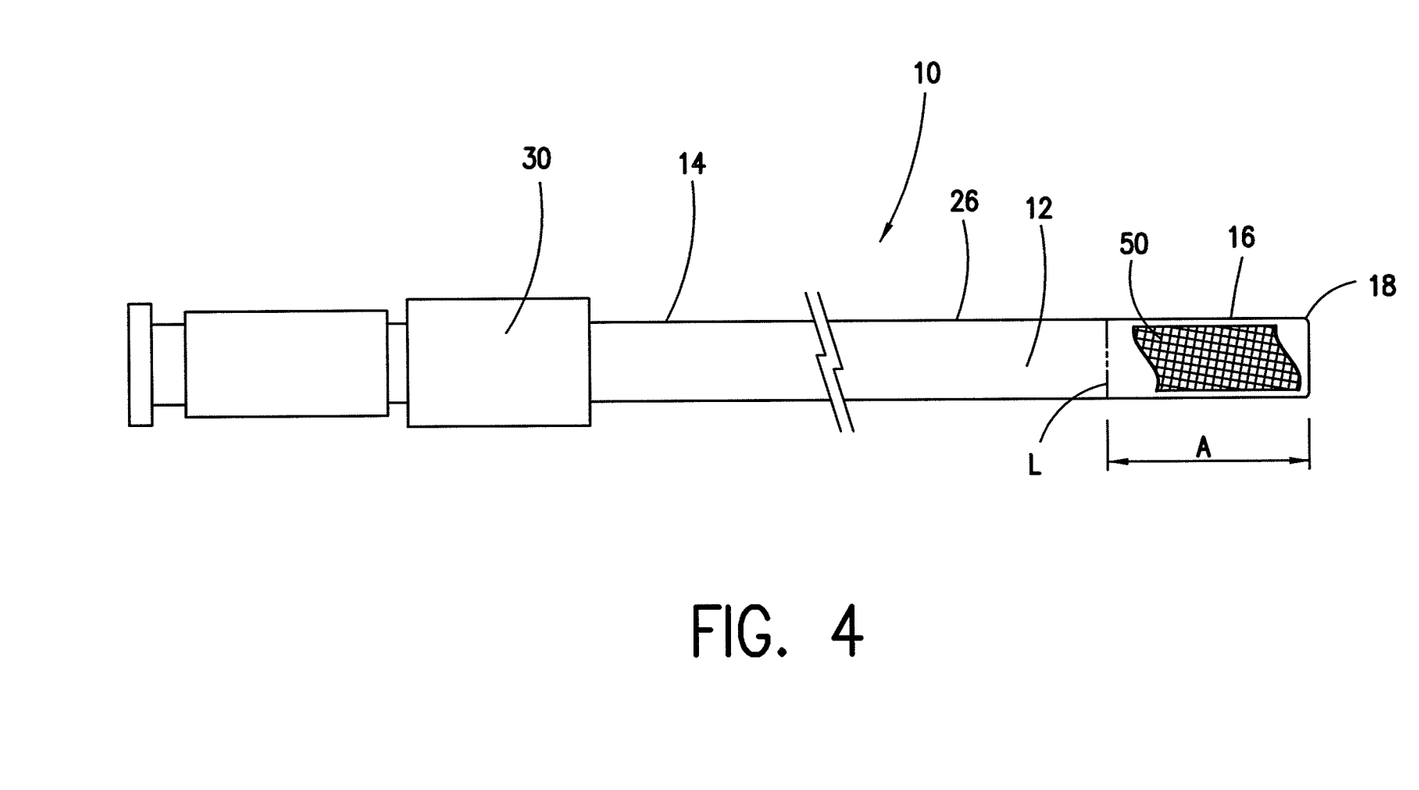
FIG. 4 is a side view of the introducer sheath wherein a portion of the sheath is broken away to show a stent residing in the nesting area of the sheath.

The nesting area of the stent 50 within the sheath body in this embodiment is indicated by "A" in FIGS. 1 and 4. Although it is preferred that the length of the coil will be the same as, or substantially the same as, the length of the underlying stent, this is not required. For example, with particularly long stents, the length of the stent may extend beyond line "L" in the proximal direction. However, it is assumed that such extension will not exceed more than about 5-10 cm beyond line "L" in most instances, and as stated, will typically not extend at all proximal to line "L". Similarly, the length of the stent 50 need not extend to line "L" in all instances. This arrangement would typically occur when a shorter stent is positioned within the sheath, such as a coated stent. Optimally, however, it is preferred that the sheath is constructed such that the length of the stent or other device to be housed therein for deployment will have a length substantially the same as the length of the coil portion of the sheath. To provide greater versatility for the use of sheath 10, however, this relationship need not necessarily be present for every possible use of sheath 10.

Due to the inherent structure of the braid, e.g. made up of woven filaments, a braid is less susceptible to axial stretching than a coil. Even though a braid may exhibit a certain amount of stretching upon withdrawal, the stretching is generally less than that exhibited by a coil of comparable length and composition. As a result, the ability of the sheath wall to withstand the radial expansive forces exerted by the stent on the interior of the wall of the sheath is generally not diminished in the manner experienced with a (stretched) coil reinforcement.

Although the use of a braid reinforcement reduces the likelihood of stretching of the sheath upon withdrawal, along with the concomitant diminution of reinforcing ability, a braided sheath has a tendency to radially constrict somewhat when axially stretched. Generally, this is not a problem when a PTFE inner liner is utilized with stents having a length of, e.g., about 50 mm or less. However, as longer stents are used, and as other stent compositions and coatings are employed, any such constriction may become more significant, and may hinder smooth deployment of the stent. Since constriction of a sheath reduces its effective inner diameter, the diameter of the medical interventional device that can be deployed therethrough also may be limited.

By utilizing a sheath as described herein having longitudinally adjacent braid (along the major sheath length) and coil (at the distal end) reinforcements, the overall stretching of the sheath upon deployment of the stent is reduced when compared to a prior art sheath having a coil reinforcement along its entire length. Similarly, since the coil is provided at the distal portion of the sheath, and preferably only at that portion of the sheath within which the stent is nested, a radial constriction that might otherwise result from the presence of the braid does not significantly occur in the area of the stent. Thus, the benefits of each type of reinforcement are realized, and the disadvantages attendant to the use of each type of reinforcement is minimized.

Introducer sheath 10 may be formed to have any length required to fulfill its intended purposes. In most cases, the sheath will have a length between about 40 and 125 cm, and most generally, between about 70 and 100 cm. Generally, the lengths of inner liner 20 and outer jacket 26 are the same. For an exemplary sheath of 70-100 cm length, the distal portion, for example the distal 30-60 cm, may be covered with a conventional hydrophilic coating, such as AQ® hydrophilic coating. In addition, if desired, outer jacket 26 can comprise two or more discrete longitudinal segments of differing durometer. Making the distal portion of the outer jacket from a lower durometer material than that from which the proximal portion is made yields a tubular member 12 whose distal portion is more flexible than the proximal portion. This arrangement is described in greater detail in the incorporated-by-reference Patent Publication No. 2001/0034514.

Figure 3:
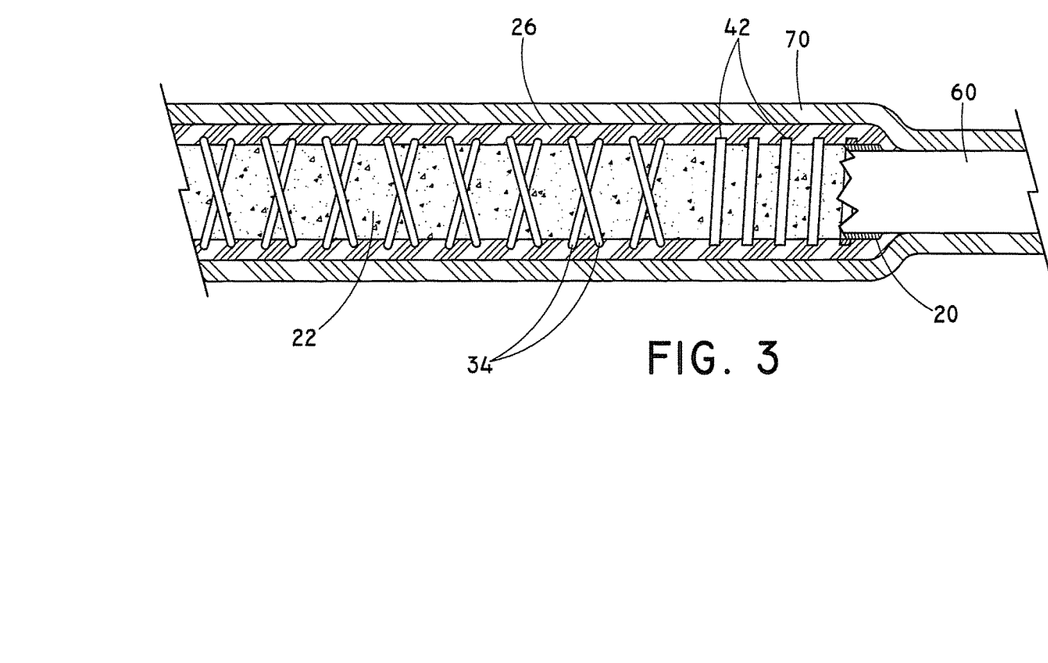
FIG. 3 is a side view, partially in section, illustrating the introducer sheath disposed over a mandril, and enveloped in a heat shrink tube during preparation of the sheath.

An introducer sheath 10 according to the present invention may be constructed in the following manner. Initially, the inner liner 20 is placed on a suitably-sized mandril 60 (FIG. 3). Generally, the mandril will have an outer diameter substantially the same as the inner diameter of the inner liner to insure a close tolerance between the two. A braid is cut to a length such that the braid will extend along about 90% of the length of the sheath body. Preferably, the distal end of the braid is pre-treated to control fraying. This may be accomplished, e.g., by heat shrinking fluorinated ethylene propylene (FEP) around the end of the braid prior to cutting. This is believed to allow for a more even cut, while also preventing the braid ends from fraying. After the FEP is removed, the braid is slid over the liner at one side (proximal) of the mandril. The coil is transferred over the distal end of the mandril. As stated, the relative ratio of the length of the braid to that of the coil in this preferred embodiment is preferably about 9:1.

The outer jacket material 26 is then slid over the mandril/liner/reinforcements (braid+coil), and the entire assembly is placed in a heat shrink envelope 70. Heat shrink enclosures for use in forming medical devices are well known in the art, with fluorinated ethylene propylene (FEP) being a preferred composition for use herein. Those skilled in the art will appreciate that various alternative compositions for the heat shrink envelope would also be suitable for use in forming this sheath, as long as the melt temperature of the material used for the outer jacket is lower than that of the heat shrink enclosure. The heat shrink enclosure and contents are placed in an oven and heated (typically at about 385° F. (196° C.)

when FEP is used as the heat shrink and a polyether block amide is used as an outer jacket material) for a suitable period of time to melt the outer jacket material such that it flows between the braid filaments and the coil turns as described. After removal from the oven, the entire assembly is cooled, and the FEP envelope 70 is cut away.

The dimensions (for example, the thickness) of the various elements mentioned above should be selected in view of the proposed use of the introducer sheath 10. It is believed that the selection of such dimensions will lie within the level of skill in the art, once benefit of the present disclosure is had. While a modest amount of trial-and-error may be needed to obtain optimal dimensions, it is believed that any required experimentation will not be undue.

Details of the construction or composition of the various elements of the introducer sheath 10 of the present invention not otherwise disclosed are not believed to be critical to the present invention, so long as the recited elements possess the strength or mechanical properties needed for them to perform as required. Many such details not described herein are recited in detail in the incorporated-by-reference U.S. Pat. No. 5,380,304, and U.S. Patent Publication No. 2001/0034514. Additional details of construction are believed to be well within the ability of one of ordinary skill in the art.

When used for delivering a medical interventional device, such as a stent, to a target site in a body passageway of a patient, the interventional device is loaded into the distal portion of the introducer sheath. Preferably, the interventional device is loaded into nesting area "A", shown in FIG. 1. The distal end 18 of the introducer sheath is initially inserted through a body opening previously formed, e.g., by the well-known Seldinger technique. The introducer sheath is advanced, typically over a wire guide (not shown) through the body passageway until the distal end 18 reaches the target site. The sheath is then slowly withdrawn, while an inner catheter, such as a conventional obturator or pusher (not shown), disposed in the lumen of the inner liner obstructs the stent from being withdrawn with the sheath. As a result, the interventional device is slowly pushed out of the distal end of the sheath as the sheath is withdrawn from the target site. As the interventional device becomes free of the constraints imposed upon it by the sheath, the device expands to the diameter of the body passageway, such as a blood vessel.

It is therefore intended that the foregoing detailed description be regarded as illustrative rather than limiting, and that it be understood that it is the following claims, including all equivalents, that are intended to define the spirit and scope of this invention.

The invention claimed is:

1. A medical assembly, comprising:
   an introducer sheath comprising a tubular inner liner having a proximal portion, a distal portion, and an outer surface, said inner liner having a passageway extending therethrough; a first reinforcing element positioned along said outer surface of said inner liner, said first reinforcing element disposed at said proximal portion of said inner liner and extending in a distal direction therefrom, said first reinforcing element comprising a braid formed of a plurality of interwoven filaments, said braid having a length that extends at least 70% of a length of the introducer sheath; a second reinforcing element positioned longitudinally adjacent to said first reinforcing element along said outer surface of said inner liner, said second reinforcing element comprising a helical coil, said helical coil having a plurality of coil turns, and having a length that does not exceed 30% of a length of the sheath, wherein a proximal end of said coil is positioned distal to a distal end of said braid; and an outer jacket positioned longitudinally around said first and second reinforcing elements, and connected to the outer surface of said inner liner between said interwoven filaments and said coil turns; and
   an expandable stent housed within said passageway at said coil for deployment to a target site within a body passageway of a patient, said stent exerting an outward force upon said introducer sheath along a length of said stent, said stent thereby radially expanding to a diameter of said body passageway upon withdrawal of said introducer sheath;
   wherein said length of said coil is substantially equal to said length of said stent, said braid resisting axial stretching during withdrawal of said introducer sheath, and said coil resisting radial constriction of said stent during withdrawal of said introducer sheath.

2. The medical assembly of claim 1, wherein said braid length extends at least 90% of the length of the introducer sheath, and said coil length does not exceed 10% of the length of the introducer sheath.

3. The medical assembly of claim 1, wherein said braid comprises round wire, and said coil comprises flat wire.

4. The medical assembly of claim 1, wherein said tubular inner liner comprises PTFE having a roughened outer surface, and said outer jacket comprises a polyamide, said polyamide being bonded to said roughened outer surface.

5. The medical assembly of claim 1, wherein said length of said stent is greater than 80 mm.

6. The medical assembly of claim 1, wherein said length of said stent is greater than 100 mm.

7. A method of delivering an expandable stent to a target area in a body passageway of a patient, comprising:
   providing an introducer sheath, said introducer sheath comprising a tubular inner liner having a proximal portion, a distal portion, and an outer surface, said inner liner having a passageway extending therethrough, said passageway sized for receiving said stent therein; a first reinforcing element positioned along said outer surface of said inner liner, said first reinforcing element disposed at said proximal portion of said inner liner and extending in a distal direction therefrom, said first reinforcing element comprising a braid formed of a plurality of interwoven filaments, said braid having a length that extends at least 70% of a length of the introducer sheath; a second reinforcing element positioned longitudinally adjacent and distal to said first reinforcing element along the outer surface of the inner liner, said second reinforcing element comprising a helical coil having a plurality of coil turns, said helical coil having a length substantially equal to a length of said stent; and an outer jacket positioned longitudinally around said first and second reinforcing elements, and connected to the outer surface of said inner liner between said interwoven filaments and said coil turns;
   positioning said stent in said passageway at said distal portion of said inner liner interiorly of said helical coil, said stent exerting an outward force upon said introducer sheath along said length of said stent;
   inserting said sheath into said body passageway such that a sheath distal end portion is disposed at said target area; and
   delivering said stent to said target area from said sheath distal end portion by withdrawing said introducer sheath from said stent, said braid resisting axial stretching during withdrawal of said introducer sheath, and said coil resisting radial constriction of said stent during withdrawal of said introducer sheath, said stent radially expanding to a diameter of said body passageway upon withdrawal of said introducer sheath.

8. The method of claim 7, wherein said braid extends at least 90% of a length of the introducer sheath, and wherein said coil begins substantially at a distal end of said braid and extends distally therefrom.

9. The method of claim 8, wherein said inner liner comprises PTFE having a roughened outer surface, and said outer jacket is bonded to said roughened outer surface of said inner liner.

10. The method of claim 7, wherein inner liner comprises PTFE, said sheath further comprising a radiopaque marker disposed at said sheath distal end portion, and having a hydrophilic coating over at least said sheath distal end portion.

11. An assembly comprising:
an expandable stent; and
an introducer sheath, said introducer sheath comprising a tubular inner liner having a proximal portion, a distal portion, an outer surface, and a passageway extending therethrough; a first reinforcing element and a second reinforcing element disposed along said outer surface of said inner liner, said first reinforcing element comprising a braid and said second reinforcing element comprising a coil, said braid disposed at said proximal portion of said inner liner and extending distally therefrom, said coil disposed at said distal portion longitudinally adjacent said braid, said braid having a length that extends at least 70% of a length of the sheath, said coil having a length that does not exceed 30% of a length of the sheath, said coil defining a nesting area for housing said stent prior to a deployment thereof; and an outer jacket positioned longitudinally around said reinforcing elements and connected to said outer surface of the inner liner, said stent exerting an outward force upon said introducer sheath along a length of said stent, said stent thereby radially expanding to a diameter of said body passageway upon withdrawal of said introducer sheath;
wherein said length of said coil is substantially equal to said length of said stent, said braid resisting axial stretching during withdrawal of said introducer sheath, and said coil resisting radial constriction of said stent during withdrawal of said introducer sheath.

12. The assembly of claim 11, wherein said braid extends at least 90% of the length of the sheath, and wherein said coil begins substantially at a distal end of said braid and extends to a distal end of said sheath.

13. The assembly of claim 11, further comprising a radiopaque marker disposed along said sheath length distal to said braid.

14. The assembly of claim 11, wherein said inner liner comprises a lubricious fluoropolymer.

15. The assembly of claim 14, wherein said lubricious fluoropolymer comprises PTFE, and wherein said inner liner has a substantially uniform inner diameter ranging up to 30 French.

16. The assembly of claim 15, wherein the tubular inner liner has a roughened outer surface, and wherein said outer jacket is bonded to said inner tubular liner at said roughened outer surface.

17. The assembly of claim 11, wherein the outer jacket comprises at least two discrete longitudinal segments differing in durometer from a higher durometer proximal segment to a lower durometer distal segment.

18. The assembly of claim 11, wherein said outer jacket comprises a heat formable polyamide material.

19. The of assembly claim 11, wherein at least the distal end of the outer surface of the sheath is coated with a hydrophilic compound.

20. The assembly of claim 11, wherein said braid comprises round wire, and said coil comprises flat wire.

* * * * *